(12) United States Patent
Kissel et al.

(10) Patent No.: US 8,523,880 B2
(45) Date of Patent: Sep. 3, 2013

(54) MEDICAL CLIP AND APPARATUS FOR THE APPLICATION OF SUCH A CLIP

(75) Inventors: Christian Kissel, Weingarten (DE); Harald Fischer, Weingarten (DE)

(73) Assignee: Forschungszentrum, Karlsruhe, GmbH, Karlsruhe (DE)

( * ) Notice: Subject to any disclaimer, the term of this patent is extended or adjusted under 35 U.S.C. 154(b) by 1640 days.

(21) Appl. No.: 10/837,281

(22) Filed: Apr. 30, 2004

(65) Prior Publication Data

US 2004/0204724 A1 Oct. 14, 2004

Related U.S. Application Data

(63) Continuation-in-part of application No. 10/733,165, filed on Dec. 11, 2003, now abandoned.

(30) Foreign Application Priority Data

Dec. 19, 2002 (DE) .................. 102 59 411

(51) Int. Cl.
*A61B 17/10* (2006.01)
*A61B 17/08* (2006.01)
*A61B 17/04* (2006.01)

(52) U.S. Cl.
USPC ........... 606/139; 606/142; 606/151; 606/157; 606/232

(58) Field of Classification Search
USPC ......... 606/221, 151, 142, 143, 213, 152–158, 606/232
See application file for complete search history.

(56) References Cited

U.S. PATENT DOCUMENTS

| | | | | |
|---|---|---|---|---|
| 3,616,497 A * | 11/1971 | Esposito, Jr. | .................... | 24/542 |
| 3,682,180 A * | 8/1972 | McFarlane | .................... | 604/174 |
| 5,217,030 A * | 6/1993 | Yoon | .................... | 128/898 |
| 5,242,456 A * | 9/1993 | Nash et al. | .................... | 606/142 |
| 5,441,509 A * | 8/1995 | Vidal et al. | .................... | 606/151 |
| 5,474,567 A * | 12/1995 | Stefanchik et al. | ........... | 606/143 |
| 5,674,231 A * | 10/1997 | Green et al. | .................... | 606/142 |
| 5,891,155 A * | 4/1999 | Irie | .................... | 606/108 |
| 5,916,224 A * | 6/1999 | Esplin | .................... | 606/151 |
| 5,984,933 A * | 11/1999 | Yoon | .................... | 606/148 |
| 6,015,417 A * | 1/2000 | Reynolds, Jr. | .................... | 606/151 |
| 6,051,007 A * | 4/2000 | Hogendijk et al. | .................... | 606/151 |
| 6,179,849 B1 * | 1/2001 | Yencho et al. | .................... | 606/153 |
| 6,428,548 B1 * | 8/2002 | Durgin et al. | .................... | 606/142 |
| 6,579,304 B1 * | 6/2003 | Hart et al. | .................... | 606/207 |
| 6,818,009 B2 * | 11/2004 | Hart et al. | .................... | 606/232 |
| 2001/0039436 A1 * | 11/2001 | Frazier et al. | .................... | 606/219 |
| 2003/0153946 A1 * | 8/2003 | Kimblad | .................... | 606/213 |

* cited by examiner

*Primary Examiner* — Darwin Erezo
*Assistant Examiner* — Jing Ou
(74) *Attorney, Agent, or Firm* — Klaus J. Bach

(57) ABSTRACT

In a medical clip consisting of a platelet of an elastic biocompatible material, the platelet is provided with a central H-shaped cut-out so as to form a frame structure with tongues extending from the frame structure toward each other and having adjacent front edges forming grasping elements, and the frame structure is curved and elastically biases the front edges toward each other.

10 Claims, 5 Drawing Sheets

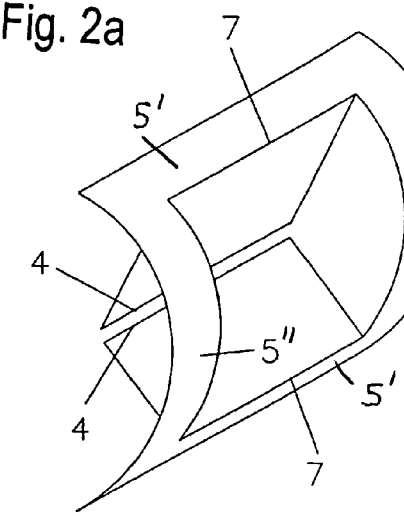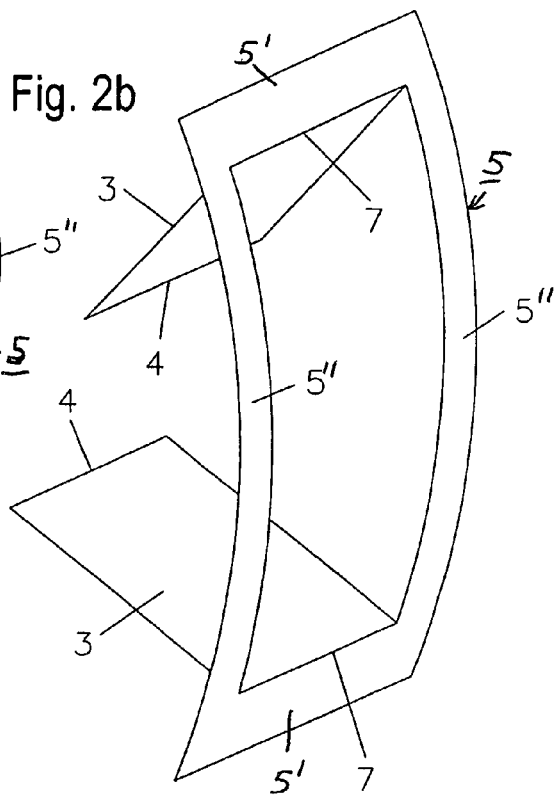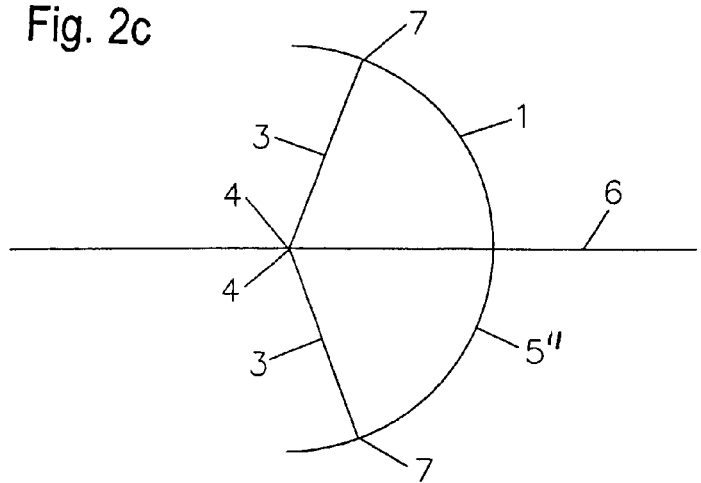

MEDICAL CLIP AND APPARATUS FOR THE APPLICATION OF SUCH A CLIP

This is a continuation-in-part application of application Ser. No. 10/733,165 filed Dec. 11, 2003 now abandoned.

BACKGROUND OF THE INVENTION

The invention relates to a medical clip comprising a curved platelet of an elastic bio-compatible material.

In the field of surgery, various types of medical clips and apparatus for the application of such clips are known. They are designed particularly for pinching off vessels and for holding together wounds, but also for fixing various implants in a human body. In comparison with other surgical procedures available for this purpose, particularly suturing, the use of a clip has the advantage that it requires comparatively little time for its application.

This is of great importance for example for the closing of a heavily bleeding wound such that the success of such a procedure overshadows all the disadvantages of clip procedures such as for example high local stresses of the tissue being pinched by the clip or the danger of additional injuries caused by the clip applied to the tissue.

There are different medical clips such as elastically and plastically deformable clips, single and multi-part clips and lockable and non-lockable medical clips.

The present invention relates to a one-piece elastically deformable clip without locking means. Such a clip includes in principle the features of a clamp that is it consists essentially of two grasping elements which are pre-tensioned and act against each other and which can be elastically opened for application to a patient.

The special advantage of such an arrangement resides in the fact that such a clip is reversibly usable that is it can be removed after application simply by bending the clip open.

DE 41 10 12 123 A1 discloses an elastic clip for holding open wounds together and, also an apparatus for the application of such a clip. The clip has essentially the form of a wire-like clamp and is bent open elastically for application so that its two ends then compress the tissue around the wound to be closed. Upon application, the two edges of a wound are compressed elastically by the force of the clamp. With teeth formed on the clamping arms, the clamp is prevented from slipping out of the tissue. The elastic clamp is in this way designed for firm clamping and is usable for the reversible applications mentioned above only in a limited way.

It is the object of the present invention to provide a single-piece elastically deformable medical clip without locking means as well as an apparatus for its application, which apparatus does not have the above referred to limitations concerning a reversible use. It is furthermore an object of the invention to provide an apparatus for the application of medical clips, which can store several clips for a serial application of the clips.

SUMMARY OF THE INVENTION

In a medical clip consisting of a platelet of an elastic bio-compatible material, the platelet is provided with a central H-shaped cut-out so as to form a frame structure with tongues extending from the frame structure toward each other and having adjacent front edges forming grasping elements, and the frame structure is curved and elastically biases the front edges toward each other.

The clip merely engages the tissue and reliably fixes the tissues without piercing the tissue. Furthermore, the clip can be clamped onto a thread or other object.

Preferably, the clip consists of a platelet of a memory alloy, for example, and is cut by erosion or laser procedures. The clip is removable by means of pliers.

The invention will become more readily apparent from the following description of preferred embodiments thereof on the basis of the accompanying Drawings:

BRIEF DESCRIPTION OF THE DRAWINGS

FIGS. 2a, 2b and 2c show a first embodiment of a clip formed from the platelet of FIG. 1 in a tension-free and in a tensioned configuration and also shows the clip engaging a thread.

DETAILED DESCRIPTION OF DIFFERENT EMBODIMENTS

Figure 5A:
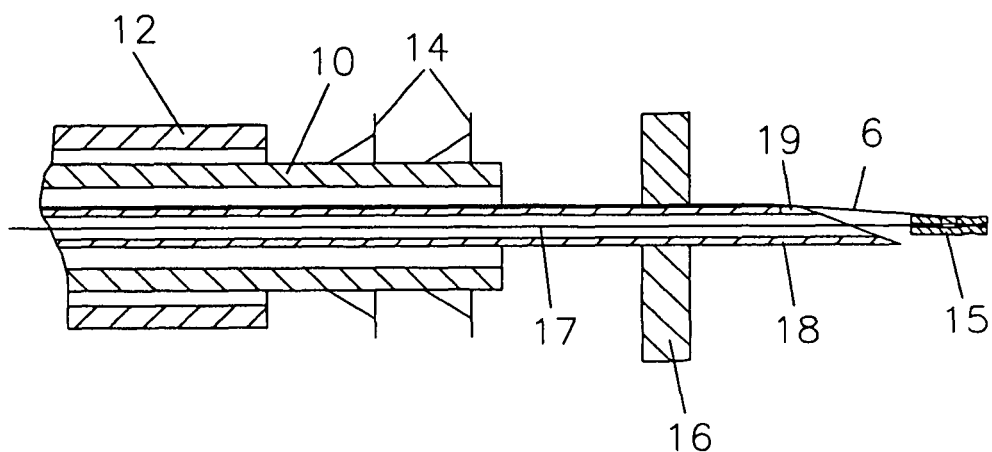
FIGS. 5a and 5b show an arrangement according to FIG. 4a with additional equipment for the clip application and a particular clip application holding a thread provided with a T-anchor.

For the application of the thread 6, a hollow needle 18 with an inclined front edge cut is inserted into the tube 10. The hollow needle 18 is provided at its end with an open slot 19. The T-anchor is contained in the hollow needle 18 and the thread 6 extends in the embodiment described from the T-anchor through the slot 19 into the space between the hollow needle 18 and the tube 10. If the hollow needle 18 has a sufficiently large inner diameter, the thread may also extend through the needle. In this case, the open slot 19 would not need to be provided. Furthermore, a guide wire 17 is disposed in the hollow needle 18 for the application of the T-anchor. The end of the guide wire 17 extends into the bore in the T-anchor for pushing it out of the needle in the desired position. FIG. 5a shows the hollow needle 18 piercing the tissue 16 with the T-anchor 15 already pushed out of the needle 18 by the guide wire 17. Subsequently, the hollow needle and the guide wire 17 and then the thread 6 are pulled back into the tube 10 whereby the thread is tensioned and the T-anchor is pivoted into a transverse position so as to be anchored in the tissue 16. The clip 14 is then slipped onto the tensioned thread 6 (see FIG. 5b).

An important advantage of the clip according to the invention resides in its simple design, which permits an economical manufacture thereof in large numbers. The platelet 1 as the bases of the clip is technically very simple and can easily and economically be stamped from sheets in large numbers.

Also, the cut-out 2 can be stamped out possibly when the bending of the two tongues is impressed for which process a temperature range should be selected where the bio-compatible material has a ductile stretch behavior and low rigidity. Subsequently, the clip is shaped—depending on the material—thermomechanically or in an other way to give it its final form.

For cutting the platelet 1 out of a sheet and for providing the cut-out 2, erosion and laser material treatment procedures are particularly suitable, especially with a miniaturizing of the clip.

With the shape of such a clip, the two edges of a wound or other subject matter can be readily engaged between the front edges 4 of the tongues 3, that is, they can be clamped by the grasping elements and pressed together by the compression forces generated by the bending of the frame the structure 5.

A high rigidity of the platelet 1 combined with a small dimension of the clip provide for reliable clamping with high forces, which are reproducibly adjustable in an accurate way by simple design features. It is not necessary that at least one catching element is pushed into tissue areas or that barbs are employed to prevent a disengagement of the grasping elements from the tissue.

The clamping effect of the clip can be improved by providing the front edges 4 of the tongues with a serrated structure, with a non-slip coating, with a rough surface or with corrugations. For manufacturing reasons, the transverse section of the H-shaped structure must be cut serrated if serrations are provided.

FIGS. 2a to 2c show a first embodiment of the clip wherein the tongues 3 are bent inwardly from the curved (C-shaped) bending frame structure 5. FIG. 2a shows the non-stressed clip, that is, the clip in its closed position which is curved with a large angle of curvature whereby the front edges 4 of the tongues 3 are in contact or disposed closely adjacent each other. For application, the clips must be bent open elastically against the given curvature so that the front edges 4 move away from each other (see FIG. 2b). As application apparatus, a pliers is preferably used which however is not shown in the figures. It includes two pliers engagement structures which engage the bending structures 5 synchronously and bends them open elastically.

FIG. 2c shows a preferred application of the clip of the first embodiment, wherein a thread is fixed. The two tongues are not aligned. They extent from the kink locations 7 which are not disposed on a straight line extending through the front edges 4. As a result, the front edges 4 of the tongues 3 are pushed apart when a thread 6 is pulled in the direction as shown in FIG. 2c toward the left whereas the thread is more firmly engaged when it is pulled in the opposite direction (toward the right as shown FIG. 2c). The tongue front edges then are pushed into firm engagement with each other and with the thread thereby preventing further movement of the thread. The clip therefrom not only fixes the thread reliably in one direction of movement, but permits movement of the thread in the opposite direction or tightening the connection. Furthermore, the two bending elements 5 may serve as stops, which for example abut the adjacent tissue upon receiving the end of the thread by means of the clip.

Figure 1:
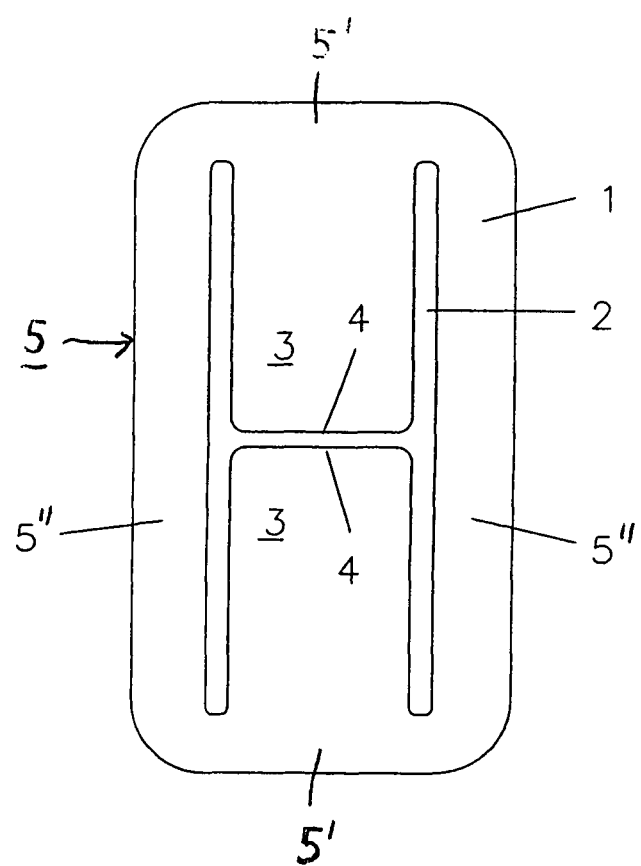
FIG. 1 shows a platelet with an H-shaped cut-out.
Figure 3A:
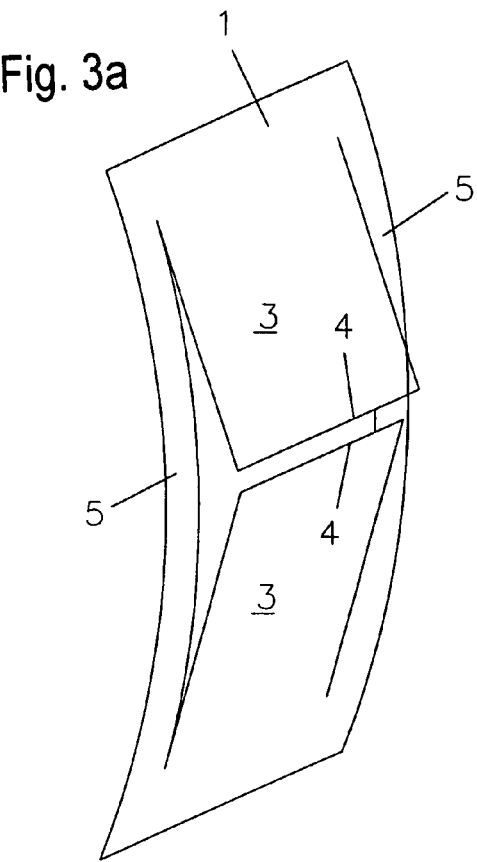
FIGS. 3a, 3b and 3c show a second embodiment of a clip formed from the platelet of FIG. 1 in a tension-free and in a tensioned configuration and also shows the clip applied to wound tissue.
Figure 3B:
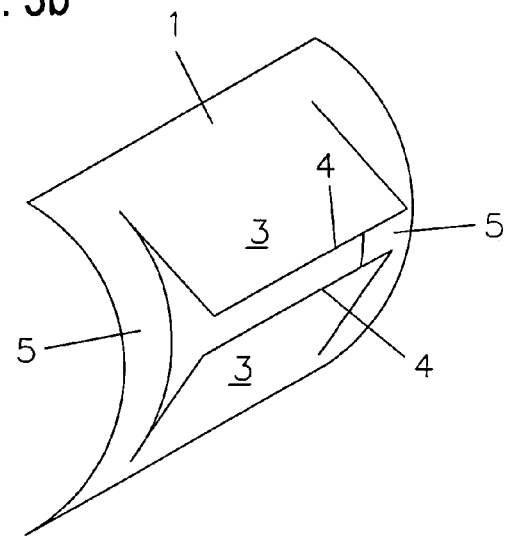
Figure 3C:
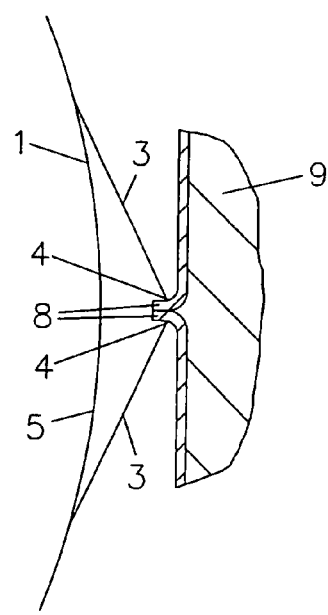

A second embodiment of the clip is shown in FIGS. 3a-3c. Here the tongues are not bent inwardly into the curved clip structure, but extend outwardly. The tongues extend either tangentially from the curved clip structure as shown in FIGS. 3a to 3c or they have defined kink areas. FIG. 3a shows the clip in a non-tensioned state, that is, the closed clip, which has a comparatively small curvature angle. In this state, the front edges 4 of the tongues 3 are disposed in close proximity. For application, the clip must first be bent further together whereby the front edges 4 of the tongues 3 move apart (see FIG. 3b). As application devices common pliers are suitable by which the clip can be compressed at its outer ends.

FIG. 3c shows the clip of the second embodiment in use as a wound clamp. The edges 8 of the wound of an organ 9 of a patient are compressed by the front edges 4 of the clip. An advantage of the embodiment is that, because of the advantageous lever ratios a relatively high clamping force is provided.

For an embodiment wherein the front edges act as knife edges the second embodiment is particularly suitable.

In this embodiment, the clip may even be used as a miniaturized cutting device for example for cutting tissue during surgery.

Figure 4A:
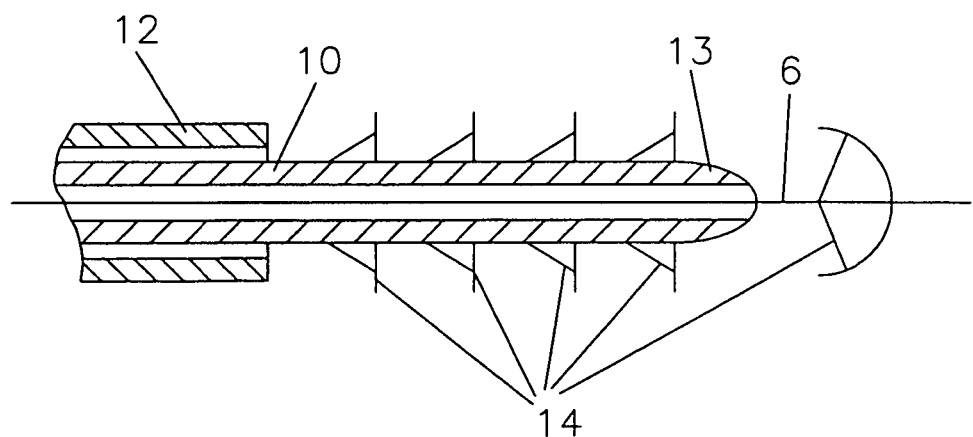
FIGS. 4a and 4b are cross-sectional views of arrangements for installing the clips.
Figure 4B:
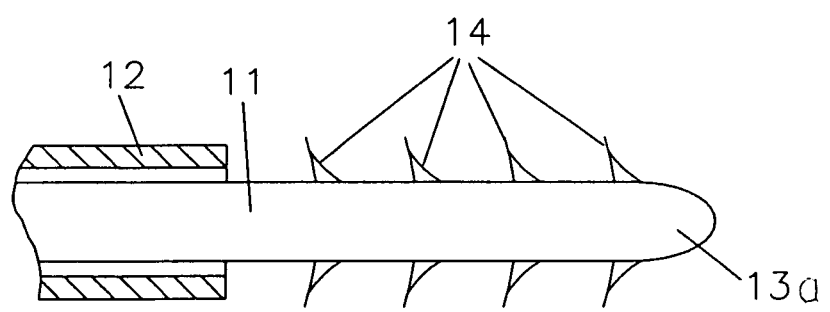

Besides, the pliers mentioned above other simple specialized application apparatus for the grasping and setting of individual clips may be used as shown in FIGS. 4a and 4b. These simple devices are magazine type structures, which receive a plurality of clips 14 for successive application.

With the two apparatus according to FIGS. 4a and 4b, the clips are bent open and disposed on a rod-like magazine member. The magazine member may be a tube 10 as shown in FIG. 4a onto which the clips of the first embodiment are slipped or a solid rod as shown in FIG. 4b onto which the clips of the second embodiment are slipped. The clips 14 slipped onto the tube 10 or rod 11 can be applied in a controlled manner one after the other by means of a slidable sleeve 12 by which the clips 14 can be moved toward the distal end 13, 13a of the tube or rod. In order to provide for a reliable separate release of each individual clip from the tube or rod, a minimum distance between adjacent clips is to be ensured. This can be achieved by rotation of the clips on the tube or rod but also by providing spacers, preferably of a resorbent material between adjacent clips. The spacers are either separate perforated discs disposed between the clips or structures formed or mounted on one side of each clip preferably on the bending structure 5, so that slipping of the clips over one another on the magazine body is prevented.

Figure 5B:
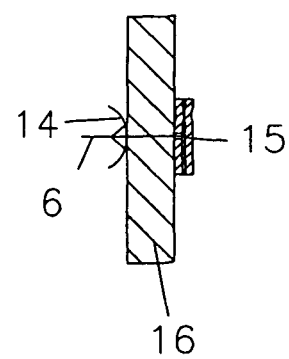

FIG. 4a shows further a thread 6 passing through the tube 10. The sleeve 12 is preferably the end of a flexible conduit and the tube 10 or rod 11 is the end of a control cable axially movably disposed in the flexible conduit (Bowden control cable). FIG. 5a shows this embodiment together with an additional device for the application of a clip 14 and a thread 6 with a T-anchor 15. A thread installed with this application device in the tissue 16 and secured by the T-anchor and a clip is shown in FIG. 5b. The T-anchor comprises a tube section with a center bore as shown in FIGS. 5a and 5b. The thread end is inserted into the center bore and is fixed to the tube section by local compression of the tube section. The tube section consists of a bio-compatible material, preferably of a material which can be resorbed.

As shown in FIG. 1 to FIG. 3c, the clip consists of a single part, that is, a platelet 1 of an elastic bio-compatible material, which is provided with an H-shaped cut-out so as to form two tongues 3 and which is curved. The two tongues 3 are bent out so as to form, with their opposite front edges 4, the grasping structure of the clip. The areas of the platelet, which are disposed at opposite sides of the two parallel line cut-outs 2 of the H-shaped cut-out and which are connected at opposite ends to the tongues 3, form a bending frame structure 5 with opposite frame end members 5' from which the tongues 3 extend and opposite frame side members 5" which provide for the elastic pre-tensioning of the grasping tongues 3 of the clip against each other. The curvature of the bending frame side members 5" of the frame structure 5 is preferably in the form of a C or a U, wherein basically all curvature angles between 0° and 180° are possible. Preferably, all the corners of the clip are rounded in order to minimize the chances of injuries by the clip.

The tube 10 may also be used for the insertion of an endoscope, which facilitates an accurate visual selection of the application area and a direct visual control of the clip application during the procedure of the minimally invasive surgery.

The apparatus according to FIGS. 4a, 4b and 5a, however are suitable only for the application of the medical clips. For the removal of the clips, for example, the pliers referred to earlier may be used.

What is claimed is:

1. A medical clip comprising a single platelet (1) of an elastic bio-compatible material, said platelet being provided with a central H-shaped cut so as to form in the platelet a frame structure (5) having side frame members 5" and end frame members (5') with flat plate-like tongues (3) surrounded by the frame structure (5) and extending from the opposite end frame members (5') toward each other and having adjacent front edges (4) oriented generally along straight parallel lines thereby forming grasping elements, and said side frame members (5") being curved in the area between the opposite end frame members (5') about an axis extending parallel to the front edges (4) of the tongues (3) and elastically biasing said front edges (4) of said plate-like tongues toward each other.

2. A medical clip according to claim 1, wherein said plate-like tongues (3) are bent inwardly from the opposite end members of said curved frame structure (5).

3. A medical clip according to claim 1, wherein the frame structure is curved so that said tongues (3) extend outwardly from said curved frame structure (5).

4. A medical clip according to claim 1, wherein said elastic biocompatible material is a shape memory material.

5. A medical clip according to claim 1, wherein the generally straight front edges (4) of said plate-like tongues (3) are serrated.

6. A medical clip according to claim 1, wherein the front edges (4) of said plate-like tongues are provided with a non-slip coating.

7. A medical clip according to claim 1, wherein the generally straight front edges (4) of said plate-like tongues are provided with a rough surface.

8. A medical clip according to claim 1, wherein the generally straight front edges (4) of said plate-like tongues are corrugated.

9. An apparatus for the application of a medical clips, each consisting of a single platelet (1) of an elastic bio-compatible material, said platelet being provided with a central H-shaped cut so as to form in the platelet a frame structure (5) having side frame members (5") and end frame members (5') with plate-like tongues (3) surrounded by the frame structure (5) and extending from the end frame mem-bers (5') toward each other and having adjacent front edges (4) forming grasping elements, said tongues (3) extending from the opposite end frame members (5') of said frame structure (5) and said side frame members (5") being curved in the area between the opposite end frame members (5') about an axis extending parallel to the front edges (4) of the tongues (3) and elastically biasing said front edges (4) of said plate-like tongues (3) toward each other, said apparatus comprising a tubular rod (10, 11) having a curved distal front end (13, 13a) and forming a magazine body onto which a plurality of said clips are slipped such that the rod (10, 11) extends through an opening of the clips formed by bending the plate-like tongues of each clip outwardly into a spaced position and holding the clips with the tongues in such spaced position such that the clips are slidingly supported on the rod (10, 11) and a sleeve (12) movably supported on said rod (10, 11) for moving said clips (14) axially off said distal end (13) of said rod (10, 11) so that the clips (14) automatically slide off the rod (10, 11) when being moved by the sleeve (12) to the distal curved front end (13, 13a) and a hollow needle (18) extending through the tubular rod (10) and a wire (17) with a T-anchor (15) disposed at its front end being disposed in the hollow needle (18) for piercing tissue (16) and further a thread (6) connected to the T-anchor, by which, after the T-anchor (15) has been pushed out of the needle (18) by the wire (17), the T-anchor can be pivoted into a transverse orientation and pulled into engagement with the tissue at the distal side thereof while a clip is applied at the opposite side of the tissue (16).

10. An apparatus according to claim 9, wherein said sleeve 12 is the end of a flexible conduit and said rod (10, 11) is the end of a control cable axially movably disposed in the flexible conduit.

* * * * *